US010278653B2

(12) United States Patent
Averina et al.

(10) Patent No.: US 10,278,653 B2
(45) Date of Patent: May 7, 2019

(54) ALERT MANAGEMENT FOR PHYSIOLOGICAL EVENT DETECTION

(71) Applicant: Cardiac Pacemakers, Inc., St. Paul, MN (US)

(72) Inventors: Viktoria A. Averina, Shoreview, MN (US); Julie A. Thompson, Circle Pines, MN (US); Pramodsingh Hirasingh Thakur, Woodbury, MN (US); Qi An, Blaine, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/473,190

(22) Filed: Mar. 29, 2017

(65) Prior Publication Data

US 2017/0281099 A1 Oct. 5, 2017

Related U.S. Application Data

(60) Provisional application No. 62/316,989, filed on Apr. 1, 2016.

(51) Int. Cl.
*A61B 5/00* (2006.01)
*A61B 5/04* (2006.01)
(Continued)

(52) U.S. Cl.
CPC ............ *A61B 5/746* (2013.01); *A61B 5/0031* (2013.01); *A61B 5/042* (2013.01);
(Continued)

(58) Field of Classification Search
CPC ... A61B 5/02055; A61B 5/746; A61B 5/7282; A61B 5/7275; A61B 5/02438;
(Continued)

(56) References Cited

U.S. PATENT DOCUMENTS 6,438,409 B1 8/2002 Malik et al.
6,662,114 B1 12/2003 Christenson et al.
(Continued)

FOREIGN PATENT DOCUMENTS

EP 1102200 A2 5/2001
WO WO-2006109072 A2 10/2006
(Continued)

OTHER PUBLICATIONS

Auricchio, A., et al., "Long-term effectiveness of the combined minute ventilation and patient activity sensors as predictor of heart failure events in patients treated with cardiac resynchronization therapy: Results of the Clinical Evaluation of the Physiological Diagnosis Funct", Eur J Heart Fail. Jun. 2014:16(6), (Mar. 17, 2014), 663-70.

(Continued)

*Primary Examiner* — Fekadeselassie Girma
(74) *Attorney, Agent, or Firm* — Schwegman Lundberg & Woessner, P.A.

(57) ABSTRACT

Systems, devices, and methods for managing alerts associated with a target physiological event such as a worsening heart failure event are described. A system may detect one or more alert onsets using an onset threshold, and one or more corresponding alert terminations using a reset threshold. Alerts may be issued corresponding to the detected alert onsets and alert terminations. The system may compare the alerts to a specified alert characteristic, and iteratively adjust the onset or reset threshold until the alerts corresponding to the adjusted onset or reset threshold satisfy the specified alert characteristic. The adjusted onset and reset thresholds may be presented to a user or a process for detecting the target physiological event.

20 Claims, 5 Drawing Sheets

(51) Int. Cl.
*A61B 5/042* (2006.01)
*G06F 19/00* (2018.01)
*G08B 21/04* (2006.01)
*G08B 29/22* (2006.01)

(52) U.S. Cl.
CPC .......... *A61B 5/04012* (2013.01); *A61B 5/686* (2013.01); *A61B 5/7275* (2013.01); *A61B 5/7282* (2013.01); *G06F 19/00* (2013.01); *G08B 21/0453* (2013.01); *G08B 29/22* (2013.01); *A61B 5/7264* (2013.01); *A61B 2505/03* (2013.01); *A61B 2505/07* (2013.01)

(58) Field of Classification Search
CPC ................ A61B 5/14532; A61B 5/742; A61B 2560/0468; A61B 5/0002; A61B 5/0006; A61B 5/0031; A61M 16/0051; A61M 2205/502; A61N 1/36514
See application file for complete search history.

(56) References Cited

U.S. PATENT DOCUMENTS

| | | | |
|---|---|---|---|
| 6,821,249 B2 | 11/2004 | Casscells, III et al. | |
| 7,223,552 B2 | 5/2007 | Hazen et al. | |
| 7,634,360 B2 | 12/2009 | Davalos et al. | |
| 7,771,954 B2 | 8/2010 | Hazen et al. | |
| 7,780,950 B2 | 8/2010 | Hazen | |
| 7,781,219 B2 | 8/2010 | Hazen et al. | |
| 8,036,735 B2 | 10/2011 | Cazares et al. | |
| 8,039,227 B2 | 10/2011 | Klein et al. | |
| 8,338,110 B2 | 12/2012 | Hazen et al. | |
| 8,394,601 B2 | 3/2013 | Klein | |
| 8,398,546 B2* | 3/2013 | Pacione | A61B 5/411 128/920 |
| 8,409,807 B2 | 4/2013 | Neely et al. | |
| 8,722,344 B2 | 5/2014 | Hazen et al. | |
| 8,853,266 B2 | 10/2014 | Dalton et al. | |
| 8,880,158 B2 | 11/2014 | Spector | |
| 9,005,904 B2 | 4/2015 | Hazen et al. | |
| 9,626,858 B2* | 4/2017 | Sloo | F24F 11/30 |
| 2003/0065409 A1 | 4/2003 | Raeth et al. | |
| 2003/0213490 A1* | 11/2003 | Righetti | A61M 16/0677 128/204.18 |
| 2005/0115561 A1* | 6/2005 | Stahmann | A61B 5/0031 128/200.24 |
| 2007/0028920 A1* | 2/2007 | Acker | A61M 16/0051 128/204.21 |
| 2007/0276270 A1* | 11/2007 | Tran | A61B 5/0022 600/508 |
| 2008/0269625 A1* | 10/2008 | Halperin | A61B 5/113 600/508 |
| 2008/0269631 A1* | 10/2008 | Denison | A61B 5/0478 600/544 |
| 2009/0124912 A1* | 5/2009 | McEwen | A61B 17/135 600/495 |
| 2009/0275848 A1 | 11/2009 | Brockway et al. | |
| 2010/0069921 A1* | 3/2010 | Miller | A61B 18/1233 606/130 |
| 2011/0082440 A1* | 4/2011 | Kimmo | A61M 5/14 604/503 |
| 2011/0282216 A1 | 11/2011 | Shinar et al. | |
| 2012/0123232 A1* | 5/2012 | Najarian | A61B 5/0022 600/345 |
| 2013/0267791 A1* | 10/2013 | Halperin | A61B 5/002 600/300 |
| 2014/0005502 A1* | 1/2014 | Klap | A61G 7/0527 600/301 |
| 2014/0203942 A1* | 7/2014 | Warmack | G08B 17/10 340/628 |
| 2015/0164438 A1* | 6/2015 | Halperin | A61B 5/746 340/573.1 |
| 2015/0236895 A1* | 8/2015 | Kay | H04L 43/045 709/224 |
| 2016/0163187 A1* | 6/2016 | Treacy | G08B 29/26 340/501 |
| 2016/0270658 A1* | 9/2016 | Ater | A61B 5/0011 |
| 2017/0177944 A1* | 6/2017 | Sloo | F24F 11/30 |
| 2017/0276662 A1* | 9/2017 | Machida | G01N 27/026 |

FOREIGN PATENT DOCUMENTS

| | | |
|---|---|---|
| WO | WO-2006118852 A2 | 11/2006 |
| WO | WO-2017172934 A1 | 10/2017 |

OTHER PUBLICATIONS

Binkley, P. F., et al., "Feasibility of using multivector impedance to monitor pulmonary congestion in heart failure patients", J Interv Card Electrophysiol;35(2), (Nov. 2012), 197-206.

Conraads, V. M, et al., "Sensitivity and positive predictive value of implantable intrathoracic impedance monitoring as a predictor of heart failure hospitalizations: the SENSE-HF trial", Eur Heart J., 32(18), (Sep. 2011), 2266-73.

Heist, E. Kevin, et al., "Rate Control in Atrial Fibrillation Targets, Methods, Resynchronization Considerations", Circulation. 2011;124:2746-2755., (2011), 2746-2755.

Thakur, Pramodsingh Hirasingh, et al., "Predictions of Worsening Heat Failure", U.S. Appl. No. 62/236,416, filed Oct. 2, 2015.

Yu, C. M, et al., "Intrathoracic impedance monitoring in patients with heart failure: correlation with fluid status and feasibility of early warning preceding hospitalization", Circulation, 112(6), (Aug. 9, 2005), 841-8.

"International Application Serial No. PCT/US2017/024775, International Search Report dated Jul. 4, 2017", 5 pgs.

"International Application Serial No. PCT/US2017/024775, Written Opinion dated Jul. 4, 2017", 6 pgs.

Xu, Qi, et al., "An Adaptive Algorithm for the Determination of the Onset and Offset of Muscle Contraction by EMG Signal Processing", IEEE Transactions on Neural Systems and Rehabilitationengineering, voi. 21, No. 1, (Aug. 15, 2012), 65-73.

"International Application Serial No. PCT/US2017/024775, International Preliminary Report on Patentability dated Oct. 11, 2018", 8 pgs.

* cited by examiner

ALERT MANAGEMENT FOR PHYSIOLOGICAL EVENT DETECTION

CLAIM OF PRIORITY

This application claims the benefit of priority under 35 U.S.C. § 119(e) of U.S. Provisional Patent Application Ser. No. 62/316,989, filed on Apr. 1, 2016, which is herein incorporated by reference in its entirety.

TECHNICAL FIELD

This document relates generally to medical systems, and more particularly, to systems, devices and methods for managing alerts for physiological event detection.

BACKGROUND

Congestive heart failure (CHF or HF) is a major health problem and affects many people in the United States alone. CHF patients may have enlarged heart with weakened cardiac muscles, resulting in poor cardiac output of blood. Although CHF is usually a chronic condition, it may occur suddenly. It may affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

In many CHF patients, elevated pulmonary vascular pressures may cause fluid accumulation in the lungs over time. The fluid accumulation may precede or coincide with worsening of HF such as episodes of HF decompensation. The HF decompensation may be characterized by pulmonary or peripheral edema, reduced cardiac output, and symptoms such as fatigue, shortness of breath, and the like.

Overview

Frequent monitoring of CHF patients and timely detection of events indicative of worsening HF (WHF) may reduce cost associated with HF hospitalization. Identification of patient at an elevated risk of developing future WHF events may help ensure timely treatment, improve the prognosis and patient outcome, and avoid unnecessary medical intervention and reduce healthcare cost.

Ambulatory medical devices may be used for monitoring HF patient and detecting WHF events. Examples of such ambulatory medical devices may include implantable medical devices (IMD), subcutaneous medical devices, wearable medical devices or other external medical devices. The ambulatory medical devices may include physiological sensors which may be configured to sense electrical activity and mechanical function of the heart. The ambulatory medical devices may deliver therapy such as electrical stimulations to target tissues or organs, such as to restore or improve the cardiac function. Some of these devices may provide diagnostic features, such as using transthoracic impedance or other sensor signals to detect a disease or a disease condition. For example, fluid accumulation in the lungs decreases the transthoracic impedance due to the lower resistivity of the fluid than air in the lungs.

Detection of a WHF event, such as a precipitating event such as increased thoracic fluid accumulation, may be based on a detected change of a sensor signal (such as a thoracic impedance signal) from a reference signal. An ideal detector of a WHF event, such as a HF decompensation event, may have one or more of a high sensitivity, a high specificity, a low false positive rate (FPR), or a high positive predictive value (PPV). The sensitivity may be represented as a percentage of actual WHF events that are correctly recognized by a detection method. The specificity may be represented as a percentage of actual non-WHF events that are correctly recognized as non-WHF events by the detection method. The FPR may be represented as a frequency of false positive detections of WHF events per patient within a specified time period (e.g., a year). The PPV may be represented as a percentage of the detected WHF events, as declared by the detection method, which are actual WHF events. A high sensitivity may help ensure timely intervention to a patient with an impending WHF episode, whereas a high specificity and a high PPV may help avoid unnecessary intervention and added healthcare cost due to false alarms.

Detection of a WHF event may involve producing one or more alerts such as to warn a healthcare provider an on-going or future impending WHF event, or to be used in automated detection of a WHF event. Alert may be issued when a physiological signal or a trend of measurements of the physiological signal crosses a threshold, and may be issued before, during, or after the WHF event. The alert threshold may affect characteristics of the alerts such as number of alerts, frequency of alerts, or alert durations. For example, improperly chosen alert threshold may result in fractured alerts or perpetual alerts. Fractured alerts may be manifested as multiple separated alerts each having relative short durations. Fracture alerts may be caused by repeated detections and loss of detections of a single underlying WHF event, and are more likely to happen when the patient's response to the underlying WHF event fluctuates. Perpetual alerts may be manifested as single sustained alert with a long duration that includes a non-WHF event, or two or more clinically distinguishable WHF events. When alerts are used to warn the healthcare provider an on-going or impending WHF event, fracture alerts may unnecessarily consume healthcare resources and increase healthcare cost, and perpetual alerts may not effectively distinguish separate WHF events. Therefore, neither fracture alerts nor perpetual alerts adequately signify the underlying WHF event. At least with these in consideration, the present inventors have recognized that there remains a considerable need for improving the techniques for alert management in applications such as WHF event detection in CHF patients.

Embodiments of the present subject matter provide systems, devices, and methods for managing alerts associated with a target physiological event such as a WHF event. A system may detect one or more alert onsets using an onset threshold and one or more corresponding alert terminations using a reset threshold. One or more alerts may be issued corresponding to the detected alert onsets and alert terminations. The system may compare the alert to a specified alert characteristic, and iteratively adjust the onset or reset threshold until the alerts corresponding to the adjusted onset or reset threshold satisfy the specified alert characteristic. The adjusted onset and reset thresholds may be presented to a user or a process for detecting a target physiological event.

In Example 1, a system for managing alerts associated with a target physiological event in a subject is disclosed. The system may include a physiological sensor circuit to sense a physiological signal from a subject, a signal processor circuit configured to generate a signal metric trend from the sensed physiological signal, and an alert management circuit coupled to the signal processor circuit. The alert management circuit may detect from the signal metric trend (1) one or more alert onsets using an onset threshold and (2)

one or more corresponding alert terminations using a reset threshold. The alert management circuit may include an alert generator circuit to issue one or more alerts corresponding to the detected one or more alert onsets and one or more alert terminations, and a parameter adjuster circuit to iteratively adjust the onset or reset threshold, which may include, when the one or more alerts fail to satisfy a specified alert characteristic, adjust the onset or reset threshold until the one or more alerts corresponding to the adjusted onset or reset threshold satisfy the specified alert characteristic; and when the one or more alerts satisfy the specified alert characteristic, determine target onset and reset thresholds for presenting to a user or a process.

Example 2 may include, or may optionally be combined with the subject matter of Example 1 to optionally include, a detector circuit that may detect a target physiological event based on the one or more alert onsets and the corresponding one or more alert terminations.

Example 3 may include, or may optionally be combined with the subject matter of one or any combination of Examples 1 or 2 to include, a user interface for generating a human-perceptible presentation of the one or more alerts including an alert number during a specified period of time, an alert duration, an indication of true alert or false alert, a count of true or false alerts.

Example 4 may include, or may optionally be combined with the subject matter of Example 3 to optionally include, the user interface that may receive the specified alert characteristic.

Example 5 may include, or may optionally be combined with the subject matter of one or any combination of Examples 1 through 4 to include, the parameter adjuster circuit that may be configured to adjust at least one of the onset or reset threshold according to a step-up or a step-down protocol.

Example 6 may include, or may optionally be combined with the subject matter of one or any combination of Examples 1 through 5 to include, the specified alert characteristic includes one or more of an alert number during a specified time period, an alert duration, an inter-alert interval, a false alert number, a true alert number, a temporal pattern of alerts, a statistical distribution of alerts during a specified time period, a statistical distribution of alert durations, a statistical distribution of false alert number or true alert number, a statistical distribution of inter-alert intervals.

Example 7 may include, or may optionally be combined with the subject matter of one or any combination of Examples 1 through 6 to include, the specified alert characteristic that may include an expected number of alerts during a specified time period, and the alert generator circuit issues a reference number of alerts corresponding to the detected alert onsets and alert terminations within the specified time period, and wherein the parameter adjuster circuit is configured to: if the expected alert number is less than the reference alert number, increase at least the onset threshold until the alert generator circuit issues the expected number of alerts; or if the expected alert number is greater than the reference alert number, decrease at least the onset threshold until the alert generator circuit issues the expected number of alerts.

Example 8 may include, or may optionally be combined with the subject matter of one or any combination of Examples 1 through 7 to include, the specified alert characteristic that may include an expected false alert number during a specified time period. The alert generator circuit may issue a reference false alert number within the specified time period, and the parameter adjuster circuit may be configured to, if the expected false alert number is less than the reference false alert number, increase at least the onset threshold until the alert generator circuit issues expected false alert number.

Example 9 may include, or may optionally be combined with the subject matter of one or any combination of Examples 1 through 8 to include, the specified alert characteristic that may include an expected true alert number during a specified time period. The alert generator circuit may issue a reference true alert number within the specified time period, and the parameter adjuster circuit may be configured to, if the expected true alert number is greater than the reference true alert number, decrease at least the onset threshold until the alert generator circuit issues expected true alert number.

Example 10 may include, or may optionally be combined with the subject matter of one or any combination of Examples 1 through 9 to include, the parameter adjuster circuit that may receive information about a known clinical event during a specified time period, adjust at least the onset threshold until the alert generator circuit issues at least one alert temporally corresponding to the known clinical event, and determine the target onset threshold as the adjusted threshold corresponding to the known clinical event.

Example 11 may include, or may optionally be combined with the subject matter of one or any combination of Examples 1 through 10 to include, the parameter adjuster circuit that may receive information about a known stable period, adjust at least the onset threshold until the alert generator circuit issues no more than a specified acceptable number of alerts within the known stable period, and determine the target onset threshold as the adjusted threshold corresponding to the specified acceptable number of alerts.

Example 12 may include, or may optionally be combined with the subject matter of Example 11 to optionally include, the specified acceptable number of alerts within the known stable period being set to zero, and the parameter adjuster circuit that may determine the target onset threshold as the smallest threshold corresponding to no alert during the stable period.

Example 13 may include, or may optionally be combined with the subject matter of one or any combination of Examples 1 through 12 to include, the parameter adjuster circuit that may receive information about a known unstable period including onset timing of the known unstable period, adjust at least the onset threshold until the alert generator circuit generates an alert substantially close to the onset timing of the known unstable period, and determine the target onset threshold as the smallest threshold corresponding to the alert substantially close to the onset timing of the known unstable period.

Example 14 may include, or may optionally be combined with the subject matter of one or any combination of Examples 1 through 13 to include, the parameter adjuster circuit that may receive information about a medical history of the subject, and determine the target onset or reset threshold based on the subject's medical history.

Example 15 may include, or may optionally be combined with the subject matter of Example 14 to optionally include, the parameter adjuster circuit that may determine the specified alert characteristic including an indication-based characteristic based on an association between the subject's medical history and expected alert characteristic, and determine the target onset or reset threshold using the indication-based alert characteristic.

In Example 16, a method for managing alerts associated with a target physiological event in a subject via an alert management system is disclosed. The method may include steps of: sensing a physiological signal; generating a signal metric trend from the sensed physiological signal; detecting from the signal metric trend (1) one or more alert onsets using an onset threshold and (2) one or more corresponding alert terminations using a reset threshold; issuing one or more alerts corresponding to the detected one or more alert onsets and one or more alert terminations; and iteratively adjusting the onset or reset threshold via the alert management system. The iterative adjustment may include, when the one or more alerts fail to satisfy a specified alert characteristic, adjust the onset or reset threshold until the one or more alerts corresponding to the adjusted onset or reset threshold satisfy the specified alert characteristic, and when the one or more alerts satisfy the specified alert characteristic, determine target onset and reset thresholds for presenting to a user or a process.

Example 17 may include, or may optionally be combined with the subject matter of Example 16 to optionally include, a method of receiving information about a known clinical event during a specified time period. The iterative adjustment of the onset or reset threshold may include adjusting at least the onset threshold until at least one alert temporally corresponding to the known clinical event is issued, and determining the target onset threshold as the adjusted threshold corresponding to the known clinical event.

Example 18 may include, or may optionally be combined with the subject matter of Example 16 to optionally include, a method of receiving information about a known stable period. The iterative adjustment of the onset or reset threshold may include adjusting at least the onset threshold until no more than a specified acceptable number of alerts is issued within the known stable period, and determining the target onset threshold as the adjusted threshold corresponding to the specified acceptable number of alerts.

Example 19 may include, or may optionally be combined with the subject matter of Example 16 to optionally include, a method of receiving information about a known unstable period including onset timing of the known unstable period. The iterative adjustment of the onset or reset threshold may include adjusting at least the onset threshold until an alert substantially close to the onset timing of the known unstable period is issued, and determining the target onset threshold as the smallest threshold corresponding to the alert substantially close to the onset timing of the known unstable period.

Example 20 may include, or may optionally be combined with the subject matter of Example 16 to optionally include, a method of receiving information about a medical history of the subject. The iterative adjustment of the onset or reset threshold may include determining the specified alert characteristic including an indication-based alert characteristic based on an association between the subject's medical history and expected alert characteristic, and determining the target onset or reset threshold using the indication-based alert characteristic.

The systems, devices, and methods discussed in this document may improve the medical technology of automated monitoring of patients with worsening heart failure (WHF). The alert management that is based on iterative adjustment of onset or reset thresholds according to specified alert characteristic, as discussed in this document, may enhance the performance and functionality of a medical system or an ambulatory medical device for monitoring heart failure patient. In certain examples, the enhanced device functionality may include fewer fractured alerts or perpetual alerts to WHF events. Fracture alerts may unnecessarily consume healthcare resources and increase healthcare cost, and perpetual alerts may not effectively distinguish separate WHF events. By reducing the fractured alerts and the perpetual alerts, the present systems and methods can reduce healthcare costs associated with management and hospitalization of heart failure patients. The systems, devices, and methods discussed in this document also allow for more efficient device memory usage, such as by storing information clinically more relevant to underlying WHF events, rather than events associated with fractured alerts or perpetual alerts. With a more efficient alert management, the device battery life can be extended, fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for managing alerts associated with a target physiological event or condition. The physiological event may include early precursors of a WHF event. That is, these events may occur well before the systematic manifestation of worsening of HF. Therefore, by detecting the precursor events, the present subject matter may provide a method and device for detecting an impending WHF event. The systems, devices, and methods described herein may be used to determine cardiac condition such as HF status and/or track progression of the cardiac condition such as worsening of or recovery from a HF event. This system may also be used in the context of alert management associated with other diseases, such as pulmonary edema, pneumonia, chronic obstructive pulmonary disease (COPD), myocardial infarction, acute renal disease, among others.

Figure 1:
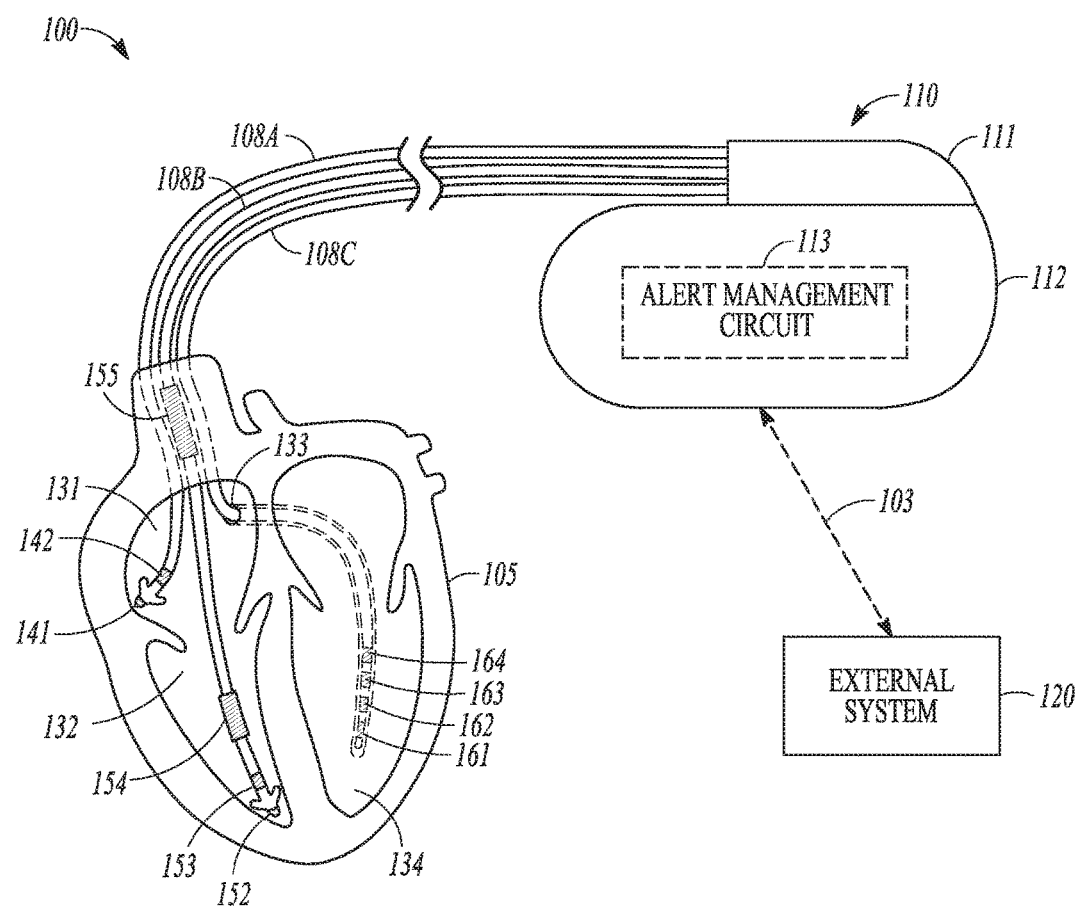
FIG. 1 illustrates generally an example of a cardiac rhythm management (CRM) system and portions of the environment in which the CRM system operates.

FIG. 1 illustrates generally an example of a Cardiac Rhythm Management (CRM) system 100 and portions of an environment in which the CRM system 100 may operate.

The CRM system 100 may include an ambulatory medical device, such as an implantable medical device (IMD) 110 that may be electrically coupled to a heart 105 such as through one or more leads 108A-C, and an external system 120 that may communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). In some examples, the CRM system may include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 may include a hermetically sealed can housing 112 that may house an electronic circuit that may sense a physiological signal in the heart 105 and may deliver one or more therapeutic electrical pulses to a target region, such as in the heart, such as through one or more leads 108A-C. The CRM system 100 may include only one lead such as 108B, or may include two leads such as 108A and 108B.

The lead 108A may include a proximal end that may be configured to be connected to IMD 110 and a distal end that may be configured to be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular electrogram and may allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161.

The electrodes 161 and 162 may be electrically connected to the IMD 110 such as via separate conductors in the lead 108C such as to allow for sensing of the LV electrogram and allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include an electronic circuit that may sense a physiological signal. The physiological signal may include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of non-limiting example and not by way of limitation. Depending on the need of the patient and the capability of the implantable device, other arrangements and uses of these leads and electrodes are contemplated.

As illustrated, the CRM system 100 may include an alert management circuit 113. The alert management circuit 113 may receive a physiological signal, such as sensed from the patient using the electrodes on one or more of the leads 108A-C or the can housing 112, or other physiological sensors deployed on or within the patient and communicated with the IMD 110. Examples of the physiological signals may include impedance signal, thoracic impedance signal, heart sounds signal, pressure signals, respiration signal, and activity signal, among others. The alert management circuit 113 may generate a signal metric from the received physiological signal, and detect from the signal metric one or more alert onsets using an initial onset threshold, and one or more alert terminations using an initial reset threshold. The alert management circuit 113 may issue one or more alerts corresponding to the detected one or more alert onsets and one or more alert terminations. The alert management circuit 113 may determine a target onset and reset thresholds by iteratively adjusting at least one of the onset or reset threshold until the one or more alerts satisfy a specified alert characteristic, such as an alert number within a specified period of time, an alert frequency, an alert duration, an inter-alert interval, a temporal pattern of the alerts, alert timing, a false alert number, or an expected statistical distribution of alerts, among others. The target onset and reset thresholds corresponding to the resulting alerts that satisfy the specified alert characteristics may be presented to a healthcare provider such as a clinician, or to a process such as a physiological event detector to detect future target physiological events. Examples of the alert management circuit 113 are described below, such as with reference to FIG. 2.

The external system 120 may allow for programming of the IMD 110 and may receive information about one or more signals acquired by IMD 110, such as may be received via a communication link 103. The external system 120 may include a local external IMD programmer. The external system 120 may include a remote patient management system that may monitor patient status or adjust one or more therapies such as from a remote location.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that may include physiological data acquisition such as using programmably specifiable sensing electrodes and configuration, device self-diagnostic test, or delivery of one or more therapies.

The alert management circuit 113, although illustrated in FIG. 1 as being implemented in the IMD 110, may alternatively be implemented in a subcutaneously implanted device, a wearable external device, a neural stimulator, a drug delivery device, a biological therapy device, or one or more diagnostic devices. In some examples, the alert management circuit 113 may be implemented in the external system 120. The external system 120 may be configured to perform WHF event detection such as using data extracted from the IMD 110 or data stored in a memory within the external system 120. The external system 120 may include a user interface that may display information about alerts and the corresponding onset and reset thresholds. In an example, portions of the alert management circuit 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
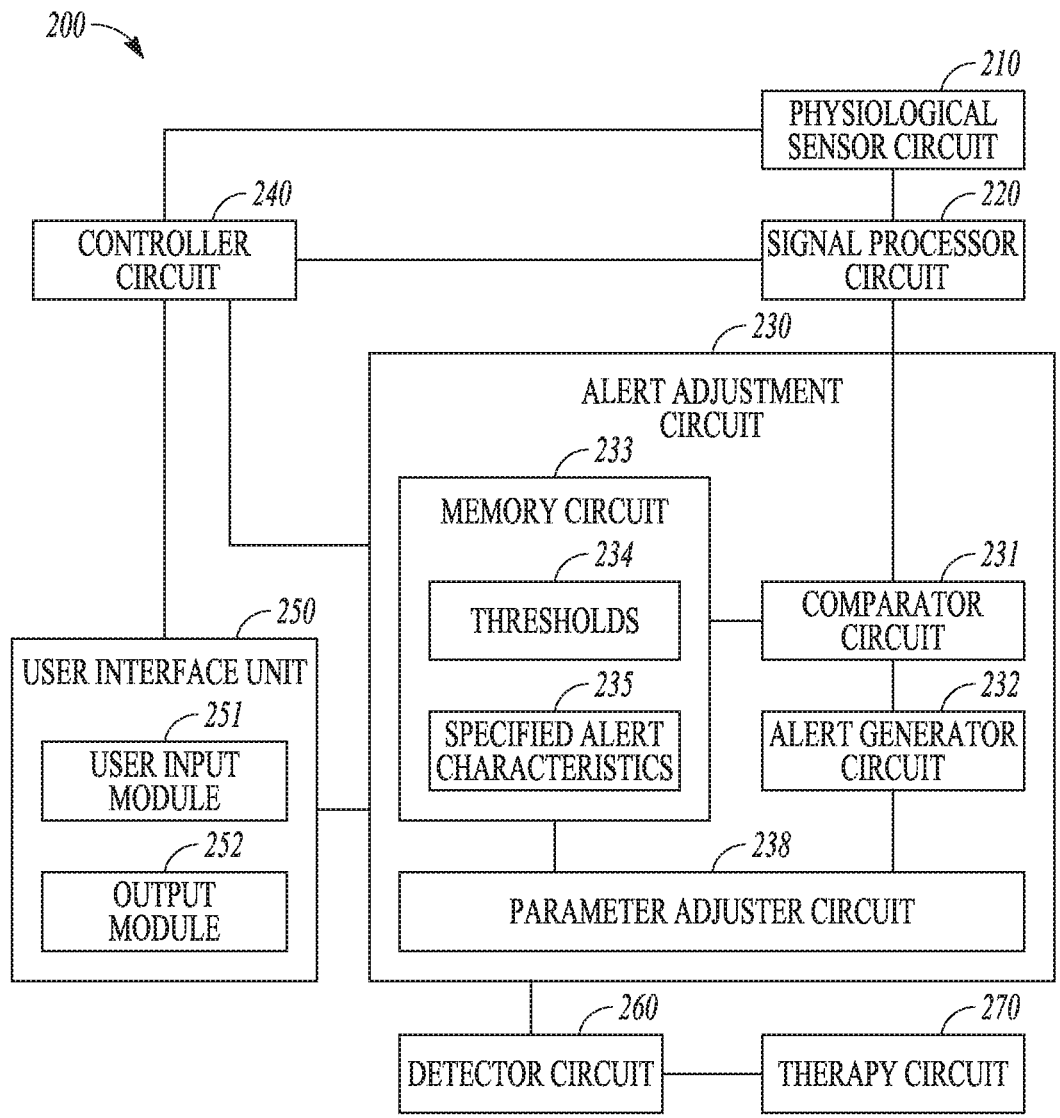
FIG. 2 illustrates generally an example of an alert management system configured to manage the alert issuance according to an alert characteristic.

FIG. 2 illustrates generally an example of an alert management system 200 that may be configured to manage the alert issuance according to an alert characteristic. The alert management system 200 may be an embodiment of the alert management circuit 113, and may include one or more of a physiological sensor circuit 210, a signal processor circuit 220, an alert adjustment circuit 230, a controller circuit 240, and a user interface unit 250.

The physiological sensor circuit 210 may include a sense amplifier circuit to sense a physiological signal from a subject, such as a physiological signal containing information indicative of status or progression of HF. In an example, the sense amplifier circuit may be coupled to one or more electrodes such as the electrodes on one or more of the leads 108A-C or the can housing 112, one or more sensors, or one or more patient monitors, where the sensing circuit may sense at least one physiological signal from the patient. The physiological sensor circuit 210 may include one or more sub-circuits to digitize, filter, or otherwise condition the received physiological signal. In an example, the physiological sensor circuit 210 may receive the one or more physiological signals from a storage device such as an electronic medical record (EMR) system, such as in response to a command signal provided by a system user, such as a clinician.

In an example, the physiological sensor circuit 210 may be coupled to one or more electrodes on one or more of the leads 108A-C or the can housing 112 to measure an impedance signal from a patient. The impedance may include a plurality of measurements of thoracic impedance or cardiac impedance. The impedance may be produced by injecting current between a first pair of electrodes and sensing the resultant voltage across a second pair of electrodes. For example, the impedance may be sensed across an RA electrode 141 or 142 and the can housing 112 ($Z_{RA\text{-}Can}$), across an RV electrode 152, 153 or 154 and a can housing 112 ($Z_{RV\text{-}Can}$), or across an LV electrode selected from electrodes 161-164 and the can housing 112 ($Z_{RV\text{-}Can}$). The impedance may include an impedance vector where the voltage sensing electrodes are the currently injection electrodes are orthogonal to each other, such as selected from RA, RV, or LV electrodes ($Z_{RA\text{-}RV\text{-}LV}$). In various examples, the physiological sensor circuit 210 may receive one or more of electrocardiograph (ECG) or electrograms (EGM) such as sensed from electrodes on one or more of the leads 108A-C or the can housing 112, a pulmonary artery pressure signal, an RV pressure signal, an LV coronary pressure signal, a coronary blood temperature signal, a blood oxygen saturation signal, a heart sound (HS) signal that includes one or more of S1, S2, S3, or S4 hear sound components, a respiration signal, or an activity signal, among others.

The signal processor circuit 220, coupled to the physiological sensor circuit 210, may include a filter circuit to filter the sensed physiological signal to produce a trend of a signal metric. The signal metric may include statistical parameters extracted from the sensed physiological signal, such as signal mean, median, or other central tendency measures or a histogram of the signal intensity, among others. Additionally or alternatively, the signal metric may include morphological parameters extracted from the sensed physiological signal, such as maximum or minimum within a specified time period such as a cardiac cycle, positive or negative slope or higher order statistics, signal power spectral density at a specified frequency range, among other morphological parameters. Depending on the types of the sensed physiological signal, examples of the signal metrics may include thoracic impedance magnitude, intensity of a heart sound component including first (S1), second (S2), third (S3) or fourth (S4) heart sound, a ratio of a S3 heart sound intensity to a reference heart sound intensity (such as S1 heart sound intensity, heart sound signal energy between R-wave and S2, or heart sound signal energy within a cardiac cycle), a respiration rate, a tidal volume, a ratio a respiration rate to a tidal volume, an activity intensity, or a time duration when the activity intensity is within a specified range or above a specified threshold, among others. In some examples, the signal metric may include composite signal metrics generated using two or more physiological signals, such as a systolic timing interval between an R-wave and a S1 heart sound within the same cardiac cycle, or an interval between S1 and S2 heart sounds within the same cardiac cycle.

The signal metric trend may be formed using multiple measurements of the signal metric during a specified period of time. In an example, the signal metric trend may include a daily trend including daily measurement of a signal metric over a specified number of days. The daily measurement may be determined as a central tendency of a plurality of measurements obtained within a day. In an example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

In some examples, the signal processor circuit 220 may process the signal metric trend and generate a predictor trend indicating temporal changes of the signal metric trend. The temporal change may be calculated as a difference between short-term values and baseline values. In an example, the short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. In some examples, the predictor trend may be determined using a linear or nonlinear combination of the relative differences between multiple short-term values corresponding to multiple first time windows and multiple baseline values corresponding to multiple second time windows, wherein the differences may be scaled by respective weight factors which may be based on timing information associated with corresponding multiple short-term window, such as described by Thakur et al., in U.S. Patent Application No. 62/236,416, entitled "PREDICTIONS OF WORSENING HEART FAILURE", which is herein incorporated by reference in its entirety.

The alert adjustment circuit 230 may be coupled to the signal processor circuit 220 to determine a target onset or reset threshold for alerts associated with a target physiological event. Examples of the target physiological events may include a WHF event or other worsening cardiac event, myocardial infarction event, a worsening pulmonary event such as a pulmonary edema or pneumonia event, or a worsening renal condition such as an acute kidney failure event, among others. In some examples, the alert adjustment circuit 230 may determine the target onset or reset threshold using the predictor trend such as generated by the signal processor circuit 220.

The alert adjustment circuit 230 may be implemented as a part of a microprocessor circuit. The microprocessor circuit may be a dedicated processor such as a digital signal processor, application specific integrated circuit (ASIC), microprocessor, or other type of processor for processing information including the physiological signals received from the physiological sensor circuit 210. Alternatively, the microprocessor circuit may be a general purpose processor that may receive and execute a set of instructions of performing the functions, methods, or techniques described herein.

In an example such as illustrated in FIG. 2, the alert adjustment circuit 230 may include circuit sets comprising one or more other circuits or sub-circuits including a comparator circuit 231, an alert generator circuit 232, a memory circuit 233, and a parameter adjuster circuit 238. These circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The comparator circuit 231 may compare the signal metric trend to an onset threshold (TO) to detect one or more alert onsets when the signal metric exceeds the TO, and to compare the signal metric to a reset threshold (TR) to detect one or more alert terminations when the signal metric falls below the TR. The thresholds TO and TR, which may be stored in the memory circuit 233, may have substantially identical values. In an example, the onset threshold TO may be greater than the reset threshold. In an example, the alert adjustment circuit 230 may receive the TO or TR from a user such as via the user interface unit 250.

The alert generator circuit 232 may issue one or more alerts corresponding to the detected one or more alert onsets and one or more alert terminations. An alert may begin at an alert onset and sustain at least up to a corresponding alert termination. The alert generator circuit 232 may generate alert characteristics, which may include temporal or statistical properties of alerts. Examples of the temporal information may include onset timing at which the signal metric trend crosses the onset threshold TO, subsequent termination timing at which the signal metric crosses the reset threshold TR, time interval between the onset and termination timings, inter-alert interval (such as from the termination timing of a previous detected event and the onset timing of a subsequent detected event). Examples of the statistical properties may include alert frequency, or false alert number, among others.

The memory circuit 233 may store the thresholds 234, which may include the onset threshold TO and the reset threshold TR. The memory circuit 233 may additionally store user-specified alert characteristics including, by way of non-limiting examples, expected or user-provided alert number, alert duration, inter-alert interval, temporal pattern of alerts, frequency of alerts, or expected statistical distribution of alert number or alert duration. In an example, the specified alert characteristics 235 may be provided by a clinician via the user interface unit 250.

The parameter adjuster circuit 238 may be coupled to the alert generator circuit 232 and the memory circuit 233, and configured to adjust the thresholds 234 until target thresholds (such as a target onset threshold or a target reset threshold) are found. In an example, the thresholds may be adjusted according to a threshold test protocol such as stored in the memory circuit 233. Examples of the threshold test protocol may include searching within a specified set of candidate thresholds, a step-up searching from a lower bound to a higher bound of threshold at a specified increment step size, or a step-down searching from a higher bound to a lower bound at a specified decrement step size, among other searching protocols.

The searching for the target thresholds may be performed iteratively. For a particular candidate threshold such as a candidate onset-reset threshold pair $(TO_i, TR_i)$, the comparator circuit 231 may detect the alert onsets and corresponding alert terminations, and the alert generator circuit 232 may generate the corresponding alert $A_i$. The parameter adjuster circuit 238 may compare the alert $A_i$ to the specified alert characteristics 235. If the alert $A_i$ fails to satisfy the specified alert characteristics 235, the parameter adjuster circuit 238 may adjust the onset or reset threshold, such as by selecting another candidate threshold from the set, or by incrementing or decrementing (according to the threshold test protocol) the present thresholds by a specified step size. The resulting adjusted thresholds $(TO_{i+1}, TR_{i+1})$ would then be used to detect the alert onsets and corresponding alert terminations at the comparator circuit 231, and an alert $A_{i+1}$ corresponding to the adjusted thresholds $(TO_{i+1}, TR_{i+1})$ may be generated by the alert generator circuit 232. The process may continue until the one or more alerts satisfy the specified alert characteristics.

When the alert (for example, $A_j$) satisfies the specified alert characteristics, the parameter adjuster circuit 238 may decide the corresponding thresholds, such as the threshold pair $(TO_j, TR_j)$, as the target onset and reset thresholds. The target thresholds $(TO_j, TR_j)$ may replace the previously stored thresholds 234 stored in the memory circuit 233, and be used by the comparator circuit 231 to detect future alerts onsets and corresponding alert terminations.

In some examples, the parameter adjuster circuit 238 may be configured to iteratively adjust only one of the onset or the reset threshold, and the other of the onset or reset threshold may be determined based on the iteratively adjusted threshold. For example, a reset threshold TR may be determined as the corresponding iteratively-adjusted onset threshold TO weighted by a scaling factor $\alpha$, that is, $TR=\alpha \cdot TO$. In an example, $0<\alpha<1$ such as the reset threshold TR is less than the corresponding onset threshold TO.

In various examples, more than one parameter adjuster circuits may be distributed among multiple devices and the external system 120 which may include a device programmer or a server in communication with the multiple devices. Each of the parameter adjuster circuits may be configured to adjust, independently or cooperatively, one or more specified alert characteristics such as provided by different users.

The controller circuit 240 may control the operations of the physiological sensor circuit 210, the signal processor circuit 220, the alert adjustment circuit 230, the user interface unit 250, and the data and instruction flow between these components. The user interface unit 250 may include a user input module 251 and an output module 252. In an example, at least a portion of the user interface unit 250 may be implemented in the external system 120. The user input module 251 may receive a user's programming input, such as regarding initial thresholds, specified alert characteristics, or threshold test protocols, among others. The user input module 251 may include an input device such as a keyboard, on-screen keyboard, mouse, trackball, touchpad, touchscreen, or other pointing or navigating devices. The input device may enable a system user to program the parameters used for sensing the physiological signals, confirming or editing a candidate or the target thresholds, adjusting the presentation of the physiological signals and detection and alerts, among others. The output module 252 may generate a human-perceptible presentation of information including the alert onsets and corresponding alert terminations, alerts associated with the physiological events, candidate or target thresholds, or other system information. The output module 252 may include a display for displaying the information. The information may be presented in a table, a chart, a diagram, or any other types of textual, tabular, or graphical presentation formats, for displaying to a system user. In an example, the presentation of the output information may include audio or other media format to alert the system user of the detected physiological events. Examples of a user interface for presenting the alerts associated with a target physiological event and user control of determining the target thresholds are discussed below, such as with reference to FIG. 3.

In some examples, the alert management system 200 may additionally include a detector circuit 260 that may detect a target physiological event based on the one or more alert onsets and the corresponding one or more alert terminations. The target physiological event may be indicative of an onset of a disease, worsening of a disease state, or a change of a disease state. The detection of the target physiological event may occur before, during, or after alert windows as defined by alert onsets and alert terminations. In an example, the detector circuit 260 may detect the target physiological event between an alert onset and a subsequent corresponding alert termination, and the target physiological event is detected if a signal metric trend exceeds a specified detection threshold. In some examples as illustrated in FIG. 2, the detector circuit 260 may be coupled to a therapy circuit 270 configured to deliver a therapy to the patient in response to the detection of the target physiological event. Examples of the therapy may include electrostimulation therapy delivered to the heart, a nerve tissue, other target tissues in response to the detection of the target physiological event, or drug therapy including delivering drug to a tissue or organ. In some examples, the therapy circuit 270 may be used to modify an existing therapy, such as adjusting a stimulation parameter or drug dosage.

Figure 3:
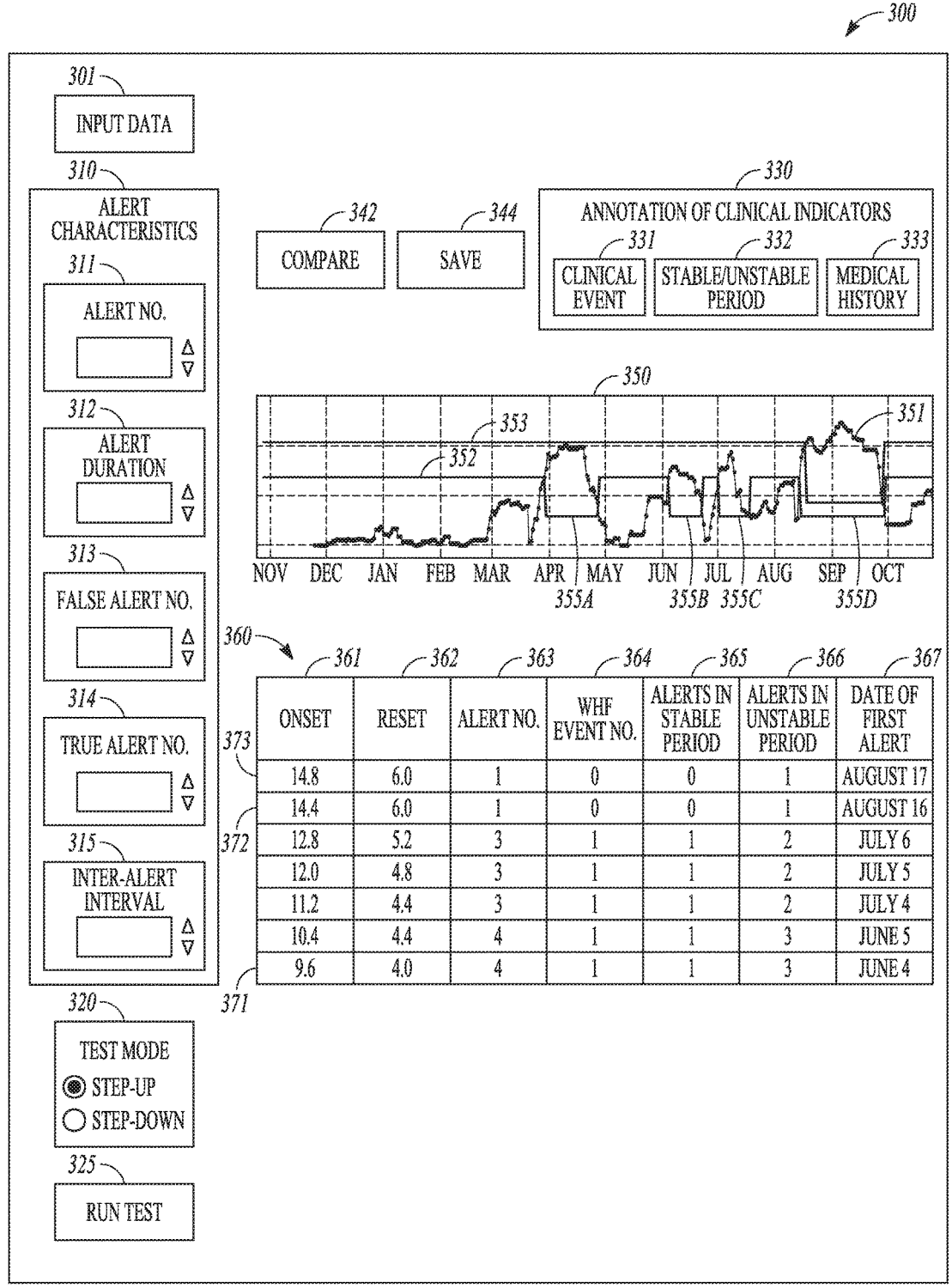
FIG. 3 illustrates generally an example of a user interface for displaying, and enabling user control of, alerts associated with a target physiological event.

FIG. 3 illustrates generally an example of a user interface 300 for displaying, and enabling user control of, alerts associated with a target physiological event. The user interface 300 may be an embodiment of at least a portion of the user interface unit 250. In an example, the user interface 300 may be a part of the external system 120.

The user interface 300 may include a display screen for displaying a plurality of control elements and textual or graphical representations. The control elements may be shown as icons or bitmaps, optionally associated with text labels or markers indicating the function or manner of operation of the corresponding control elements. The control elements may include checkboxes, push buttons, radio buttons, or other user interface controls located on the display screen. By way of non-limiting example, and as illustrated in FIG. 3, the control elements may include input data control 301 that enables a user to select and load a signal metric trend 351 for an automated threshold test. The signal metric trend 351 may be received from a signal source such as the signal processor circuit 220, the memory circuit 233, or an electronic medical record (EMR) system. The graphical representation 350 may include a display of the signal metric trend 351 once being loaded. The graphical representation 350 may additionally include display of detection result 352 based on a threshold pair, such as a nominal onset and reset thresholds.

The control elements associated with the automated threshold test may include control elements for expected alert characteristics 310, test mode selection 320, and command to run test 325. The alert characteristics control 310 enables a user to provide specified alert characteristics. The specified alert characteristics characterize an expected or desired detection performance according to the target onset and reset thresholds. By way of non-limiting example, the specified alert characteristics may include desired alert numbers 311 within a specified period of time, alert duration 312 determined as a time interval between an alert onset and subsequent alert termination, a false alert number 313 indicating the number of alerts unassociated with the target physiological event during a specified period of time such as when no target physiological event is present, a true alert number 314 indicating the number of alerts associated with the target physiological event during a specified period of time such as when the target physiological event is present, or an inter-alert interval 315 determined as the time interval between two adjacent alerts. In an example, the alert characteristic may include an alert sensitivity, such as a ratio of the number of true alerts and the number of targeted physiological events during a specified time period. Other examples of the alert characteristics may include expected statistical distributions of alert number, alert duration, inter-alert intervals, false alert number, or true alert number. For example, the alert duration is expected to follow a Gaussian distribution, or the inter-alert duration is expected to follow an exponential or Poisson distribution. The user is enabled to enter desired values or descriptors for various alert characteristics in the text box, use the control buttons to increment or decrement the exiting value shown in the text box, or select desired values from a drop-down menu that includes a list of pre-stored values.

The test mode control 320 enables a user to select between step-up and step-down protocols for running an automated threshold test. The automated threshold test session may be initiated by the user via the run test control 325. Upon completion of the threshold test, target onset and reset thresholds may be determined such as by the parameter adjuster circuit 238, and the detection result 353 corresponding to the target onset and reset thresholds may be graphically displayed along with the signal metric trend 351. The save control 344 enables a user to save the target threshold in the memory circuit 233 for future alert generation. In an example, during a threshold test session, detection result based on a candidate threshold may be graphically displayed along with the signal metric trend 351. The user may be prompted to continue or abort the remainder of the automated threshold test. The compare control 342 may enable the user to add to the graphical representation 350 additional detection results corresponding to one or more other candidate thresholds. The overlay plots of detection results, such as 352 and 353 shown in FIG. 3, provide graphical comparison of detection performances under different threshold values, such as default or nominal thresholds, user-selected candidate thresholds, or the target thresholds determined through the automated threshold test.

The user interface 300 may additionally include a presentation of threshold information, including candidate thresholds and the target thresholds, along with detection information associated with the thresholds. In an example as illustrated in FIG. 3, the presentation may be formatted in a table 360 that includes onset threshold 361, reset threshold 362, number of alerts 363 generated from the signal metric trend 351 using the corresponding thresholds 361-362, number of target physiological event such as WHF events 364 detected by using the information of generated alerts, number of alerts generated during a stable period 365 when the patient is clinically stable or during an unstable period 366 when the patient is clinically unstable, or the date of the first alert 367, among others.

A user may use a pointing device to select, highlight, move, zoom in or out, or otherwise edit a portion of the graphical representation 350 or a portion of the table 360. Examples of the pointing device may include a keyboard, an on-screen keyboard, a mouse, a trackball, a touchpad, a touch-screen, or other on-screen selection and control methods. In an example, a user may sort one of 361-367 in a specified order. A user may select from the list of the thresholds in the table 360 a target threshold pair, which may be the same or different from the target thresholds determined through the automated threshold test. The user-selected target onset and offset thresholds may be save the in the memory circuit 233, such as by activating the save control 344. In an example, alert characteristics and detection results associated with the selected target thresholds, such as one or more of 363-367, may also be saved the memory circuit 233.

In an example of generating alerts for WHF events, upon receiving user input via the user interface 300 on the expected alert characteristics 310 such as an expected number of alerts 311 ($N_{Exp}$), the comparator circuit 231 may perform detection of WHF events from the signal metric trend 351 using predetermined "nominal" onset and reset thresholds (such as row 371 of the table 360). The detection result 352, which may be graphically displayed along with the signal metric trend 351, shows four detected WHF events 355A-D. A reference number of alerts ($N_{Ref}$) corresponding to the detected WHF events within the specified time period may be generated and reported in row 371 of the table 360 ($N_{Ref}$=4). The detection parameter adjuster circuit 238 may compare the reference alert number $N_{ref}$ to the expected alert number $N_{Exp}$. If $N_{Exp}$ is less than $N_{Ref}$ (that is, fewer alerts are expected to be generated), then the detection parameter adjuster circuit 238 may increase at least the onset threshold until the comparator circuit 231 generates $N_{Exp}$ alerts. The detection parameter adjuster circuit 238 may determine the target onset threshold to be the adjusted onset threshold that corresponds to $N_{Exp}$ alerts. In an example, the target onset threshold is the smallest onset threshold that corresponds to $N_{Exp}$ alerts. On the other hand, if $N_{Exp}$ is greater than $N_{Ref}$ (that is, more alerts are expected to be generated), then the detection parameter adjuster circuit 238 may decrease at least the onset threshold until the comparator circuit 231 generates $N_{Exp}$ alerts. The detection parameter adjuster circuit 238 may determine the target onset threshold to be the adjusted onset threshold that corresponds to $N_{Exp}$ alerts. In an example, the target onset threshold is the largest onset threshold that corresponds to $N_{Exp}$ alerts. In the above example where only one alert is expected ($N_{Exp}$=1), the two threshold pairs 372 and 373 shown in table 360 would result in only one alert, thereby satisfying the specified alert characteristics. Because the onset threshold at row 372 is smaller than the onset threshold at row 373, the thresholds at row 372 may be selected as the target threshold.

In an example, a user input of an expected false alert number 313 may be received via the user interface 300. The expected false alert number may indicate the number of alerts unassociated with the target physiological event during a specified period of time such as when no target physiological event is present. A reference false alert number within the specified time period may be issued such as by the alert generator circuit 232. If the expected false alert number is less than the reference false alert number, at least the onset threshold may be increased until the expected false alert number of alerts are issued. In another example, a user input of an expected true alert number 314 may be received via the user interface 300. The expected true alert number may indicate the number of alerts associated with the target physiological event during a specified period of time such as when the target physiological event is present. A reference true alert number within the specified time period may be issued such as by the alert generator circuit 232. If the expected true alert number is greater than the reference true alert number, at least the onset threshold may be decreased until the expected true alert number of alerts are issued. In an example, the user interface 300 may receive a user input of an expected alert sensitivity, such as a ratio of the number of true alerts and the number of targeted physiological events during a specified time period. A reference alert sensitivity may be issued such as by the alert generator circuit 232. If the expected alert sensitivity is greater than the reference sensitivity, at least the onset threshold may be decreased until the expected alert sensitivity is achieved.

The user interface 300 may include one or more annotation control elements 330 that allow a user to add annotations such as clinical information of patient. By way of non-limiting example, the annotation control elements 330 may include a clinical event control 331, a stable or unstable period control 332, or patient medical history control 333. The clinical events may include known target physiological events occurred during the time segment when the signal metric trend is used for threshold test. Alternatively or additionally, the clinical events may include precursor events precipitating the target physiological event. In an example, the clinical events include presence, timing, and duration of a known WHF event. A user may activate the clinical event control 331 to annotate or mark on the graphical representation 350 the date and time of known WHF events. In some examples, events different from but clinically relevant to the target physiological events may also be annotated or marked, such as pulmonary edema, pulmonary hypertension, acute kidney failure, or other heart failure comorbidities.

The annotated clinical information, such as the annotated clinical events and the temporal information of the known clinical events, may be received by the parameter adjuster circuit 238 to generate indication-based alert characteristics, or to modify the expected alert characteristics specified by the user. For example, an alert is generally expected to be generated for the known clinical event. To determine the target thresholds for detecting the known clinical event from the signal metric trend 351, the parameter adjuster circuit 238 may adjust at least the onset threshold from a nominal value until the comparator circuit 231 generates at least one alert within the timeframe of the known clinical event. The parameter adjuster circuit 238 may then determine the target onset threshold to be the smallest threshold corresponding to the detected known clinical event. Such a choice of threshold may allow the known clinical events to be detected with the high sensitivity (which corresponds to a low onset threshold).

A user may activate the stable/unstable period control 332 to annotate or mark on the graphical representation 350 a time segment when the patient is known to be clinically stable, or a time period when the patient is known to be clinically unstable. The annotated stable or unstable period may be received by the parameter adjuster circuit 238. Generally, no alert or no more than a specified acceptable number of alerts or frequency of alerts (such as no more than one) is expected to be generated during the annotated stable period, and at least one alert is expected to be generated during the annotated unstable period. The detection parameter adjuster circuit 238 may adjust at least the onset threshold to determine the target thresholds that result in the specified number of alerts. In an example, the detection parameter adjuster circuit 238 may gradually increase the onset threshold at a specified increment step size until the comparator circuit 231 generates within the known stable period no more than the specified acceptable number of alerts. The detection parameter adjuster circuit 238 may then determine the target onset threshold to be the smallest threshold corresponding to the specified acceptable number of alerts. If no alert is expected during the stable period, the detection parameter adjuster circuit 238 may then determine the target onset threshold to be the smallest threshold corresponding to no alert during the stable period. In another example, the detection parameter adjuster circuit 238 may gradually decrease the onset threshold at a specified decrement step size until the comparator circuit 231 generates an alert earliest in time and substantially close to the beginning of the known unstable period. The detection parameter adjuster circuit 238 may determine the target onset threshold to be the smallest threshold corresponding to the earliest alert within the unstable period substantially close to the onset timing of the known unstable period.

In some examples, both a stable period and an unstable period may be marked on the graphical representation 350. The detection parameter adjuster circuit 238 may then determine the target onset threshold to be the smallest threshold that correspond to no alert or no more than the specified acceptable number of alerts in the stable period, and also correspond to the earliest alert during the unstable time period. The target thresholds may be saved to the memory circuit 233 for producing future alerts.

A user may activate the medical history control 332 to annotate events in patient medical history, such as a chronic disease, a disease classification, a previous medical procedure, a clinical lab test result, or other clinical information relevant to the target physiological events. In an example, unlike the clinical events and stable/unstable periods which may occur during the time period when signal metric trend 351 is collected and used for the automated threshold test, the events in the patient's medical history may precede the time period during which the signal metric trend is collected. Examples of events in patient medical history relevant to the WHF event may include patient renal disease, pulmonary disease, etiology of heart failure, heart failure or cardiac events, biomarkers for HF diagnosis such as Brain-Type Natriuretic Peptide (BNP) level or N-terminal pro-brain natriuretic peptide (NT-proBNP) level, left-ventricular ejection fraction, cardiac surgeries such as a coronary artery bypass grafting (CABG), or an implant of a left-ventricular assist device, among others. The parameter adjuster circuit 238 may determine the target onset or reset threshold at least based on the patient medical history. In an example, the detection parameter adjuster circuit 238 may determine the specified alert characteristics, such as the specified number of alerts $N_{Exp}$, based on a pre-determined association between the patient's medical history and the specified number of alerts during a specified time period. For example, a patient who has been annotated to have had a CABG procedure may be associated with a higher expected number of alerts $N_{Exp}$ or a higher alert frequency within a specified time period. In another example, a patient annotated to have a history of chronic kidney disease may be associated with a lower expected number of alerts $N_{Exp}$ or a lower alert frequency within a specified time period.

Although FIG. 3 provides user control for running the threshold test to determine the target onset and reset thresholds, the threshold test and determination of the target thresholds may alternatively be executed such as by the alert management system 200 with no or limited user intervention. In an example, the threshold test and determination of the target thresholds may be executed periodically or within a specified timeframe, or conditional upon a triggering event. In another example, a user may be enabled to activate or de-activate the periodic or timed update of threshold, and nominal thresholds may be used when no threshold update is to be performed.

Figure 4:
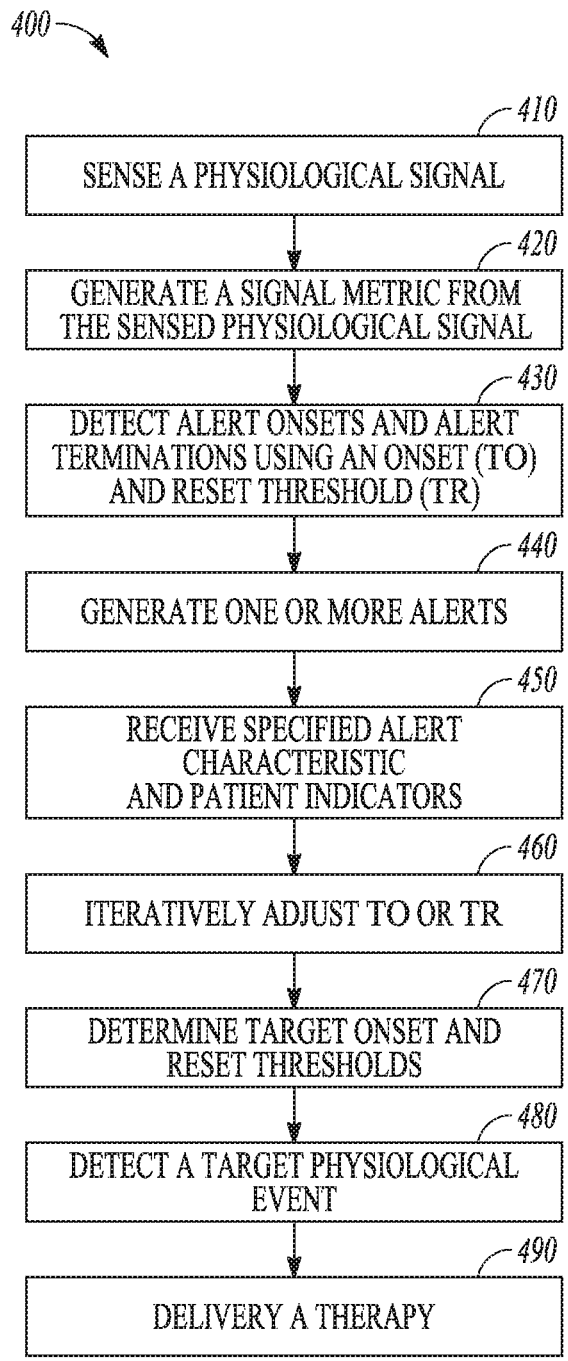
FIG. 4 illustrates generally an example of a method for managing alerts associated with a target physiological event.

FIG. 4 illustrates generally an example of a method 400 for managing alerts associated with a target physiological event. The target physiological event may include events indicative of progression of cardiac condition, such as a WHF event, a HF decompensation event, or an event indicative of recovery from a HF condition. The target event may also include pulmonary edema, pneumonia, or myocardial infarction, among others. The method 400 may be implemented and operate in an ambulatory medical device such as an implantable or wearable medical device, or in a remote patient management system. In an example, the method 400 may be executed by the alert management circuit 113 or any embodiment thereof, or by the external system 120.

The method 400 begins at 410 by sensing at least one physiological signal from a patient. Examples of the physiological signal may include one or more of an electrocardiograph (ECG) or electrogram (EGM) such as sensed from electrodes on one or more of the leads 108A-C or the can housing 112, an impedance signal, an arterial pressure signal, a pulmonary artery pressure signal, an RV pressure signal, an LV coronary pressure signal, a coronary blood temperature signal, a blood oxygen saturation signal, a heart sound (HS) signal, or a respiration signal rate signal or a tidal volume signal, among others.

At 420, a signal metric may be generated from the sensed physiological signal. The signal metric may include statistical or morphological parameters extracted from the sensed physiological signal. A signal metric trend may include multiple measurements of the signal metric during a specified period of time. In an example, the signal metric trend may include a daily trend including daily measurement of a signal metric over a specified number of days. In some examples, a predictor trend indicating a temporal change of the signal metric trend may be generated. The predictor trend may be computed as a difference between measurements of the signal metric within a short-term time window and measurements of the signal metric within a long-term time window.

At 430, one or more alert onsets and one or more alert terminations may be detected from the signal metric trend or the predictor trend, such as by using the alert adjustment circuit 230 as illustrated in FIG. 2. The detection may include a detection of an alert onset when the signal metric exceeds an onset threshold (TO), and a detection of a subsequent alert termination when the signal metric subsequently falls below a reset threshold (TR). The onset threshold TO may be substantially identical to, or alternatively may be greater than, the reset threshold TR.

At 440, one or more alerts may be generated corresponding to the detected one or more alert onsets and one or more alert terminations. An alert may be initiated upon the detection of an alert onset, and sustain up to the detected alert termination. Alert characteristics may be determined from the alerts, including timing at which the signal metric trend crosses the onset threshold TO, subsequent termination timing at which the signal metric crosses the reset threshold TR, duration between the onset and termination timing, inter-alert interval, alert frequency, false alert number, or true alert number. Alert characteristics may additionally or alternatively include statistical distributions of the alert number or alert duration, inter-alert intervals, false alert number or true alert number, among others. In an example, the distribution of the alert duration may include a Gaussian distribution, and the distribution of the inter-alert duration may include a Poisson distribution.

At 450, one or more specified alert characteristics may be received from a user input or retrieved from a memory. Examples of the alert characteristics received at 450 may include one or more of expected or user-provided alert number, alert duration, inter-alert interval, temporal pattern of alerts, frequency of alerts, or expected statistical distribution of alert number or alert duration. Additional information of patient indications may also be received at 450.

The expected alert characteristics and the patient indications, which may be provided by a clinician via the user interface 300 in FIG. 3, may be used in a threshold test for searching for target onset threshold TO or target reset threshold TR. In an example, the patient indications may include clinical events within a specified time period, such as known target physiological events or precursor events precipitating the target physiological event. For example, clinical events relevant to a target WHF event may include pulmonary events such as pulmonary edema or pulmonary hypertension, renal events such as acute kidney failure, or other heart failure comorbidities. In another example, the patient indications may include patient stability including the time periods when the patient is known to be clinically stable or unstable. In an example, the patient indications may include patient medical history relevant to the target physiological event, such as a chronic disease, a disease classification, a previous medical procedure, a clinical lab test result, or other clinical information relevant to the target physiological events. For example, relevant medical history for detecting a WHF event may include patient renal disease, pulmonary disease, etiology of heart failure, heart failure or cardiac events, biomarkers for HF diagnosis such as Brain-Type Natriuretic Peptide (BNP) level or N-terminal pro-brain natriuretic peptide (NT-proBNP) level, left-ventricular ejection fraction, cardiac surgeries such as a coronary artery bypass grafting (CABG), or an implant of a left-ventricular assist device, among others.

At 460, one or both of the onset threshold TO and the reset threshold TR may be iterative adjusted to search for target onset and reset thresholds. The threshold adjustment may follow a threshold test protocol, such as a step-up or a step-down mode each with a specified step size (the amount of increment of threshold value). The threshold test may be performed across a specified set of candidate thresholds or a specified threshold range such as defined between lower and higher bounds. If an alert corresponding to a candidate detection threshold fails to satisfy the specified alert characteristics, the onset or reset threshold may be adjusted, such as by selecting another candidate threshold, or by incrementing or decrementing the present thresholds according to the threshold test protocol. The threshold adjustment may additionally or alternatively be based on the user-provided patient indications such as known clinical events or patient stability during the time period the physiological signal used for target event detection is acquired. The threshold adjustment process continues until the alert satisfies the specified alert characteristic. When the alert satisfies the specified alert characteristics, the process of iterative threshold adjustment may terminate. At 470, the onset and reset thresholds corresponding to the resultant alert may be determined as the target onset and reset thresholds, and used for future alert generation. Examples of iterative adjustment of the onset or reset threshold are discussed below, such as with reference to FIG. 5.

The method 400 may additionally include generating a human-perceptible presentation of the alerts associated with the target physiological events, candidate or target thresholds, or other system information. The information may be presented in a table, a chart, a diagram, or any other types of textual, tabular, or graphical presentation formats, for displaying to a system user. In an example, the presentation of the output information may include audio or other media format to alert the system user of the detected physiological events.

In some examples, the method 400 may include a step 480 of detecting a target physiological event based on the one or more alert onsets and the corresponding one or more alert terminations. The target physiological event may be indicative of an onset of a disease, worsening of a disease state, or a change of a disease state. The detection of the target physiological event may occur before, during, or after alert windows as defined by alert onsets and alert terminations. In an example, the target physiological event may be detected between an alert onset and a subsequent corresponding alert termination when a signal metric trend exceeds a specified detection threshold. The method 400 may additionally include a step 490 of delivering a therapy to the patient in response to the detection of the target physiological event. Examples of the therapy may include electrostimulation therapy delivered to the heart, a nerve tissue, other target tissues in response to the detection of the target physiological event, or drug therapy including delivering drug to a tissue or organ. In some examples, at 490 an existing therapy may be modified, such as adjusting a stimulation parameter or drug dosage.

Figure 5:
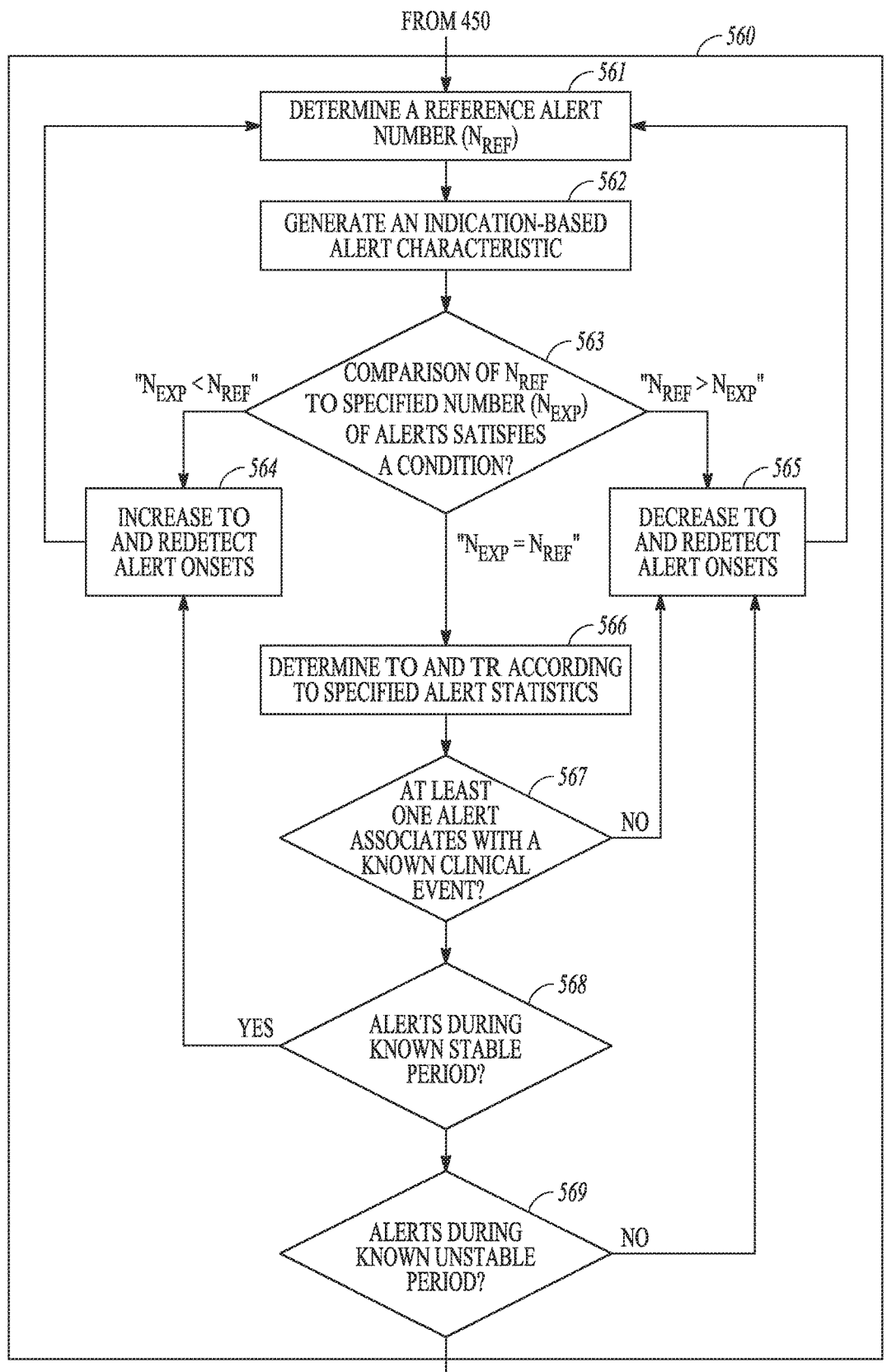
FIG. 5 illustrates generally an example of a method for iterative adjustment of an onset or reset threshold for alert management.

FIG. 5 illustrates generally an example of a method 560 for iterative adjustment of an onset or reset threshold for alert management. The method 560 may be an embodiment of the step 460 of the method 400. In an example, the method 560 may be implemented in and executed by the parameter adjuster circuit 238 as illustrated in FIG. 2.

The method 560 begins at 561 by determining a reference number ($N_{Ref}$) of alerts produced by using a predetermined "nominal" onset and reset thresholds at 430. At 562, an indication-based alert characteristic may be generated. The patient indication, such as that received at 450, may be used to automatically determine the expected alert characteristic. In an example, a pre-determined association between the patient's medical history and the alert number during a specified time period may be used to determine the expected number of alerts $N_{Exp}$. For example, a previous CABG procedure may be associated with a higher expected number of alerts $N_{Exp}$ or a higher alert frequency within a specified time period. A history of chronic kidney disease may be associated with a lower expected number of alerts $N_{Exp}$ or a lower alert frequency within a specified time period. In some examples, the indication-based alert characteristics may be used to modify a user-provided expected alert characteristic at 450.

At 563, the reference alert number $N_{Ref}$ may be compared to the expected alert number NE to determine if a specified condition is satisfied. If $N_{Ref}$ is equal to $N_{Exp}$, or falls within a specified margin of $N_{Exp}$, then at 566, the present thresholds are deemed appropriate, and no adjustment is to be made. However, if at 563 $N_{Exp}$ is less than $N_{Ref}$ (that is, fewer alerts are expected during the specified time period), then at 564 at least the onset threshold TO may be increased such as by an increment step size according to a threshold test protocol. The alert onsets detection using the adjusted thresholds may be performed on the same signal metric trend, and corresponding reference alerts may be generated at 561. The process continues until $N_{Exp}$ alerts (or within a specified margin of $N_{Exp}$) are generated. The corresponding onset and reset thresholds may be determined at 566. In an example, the largest onset threshold that corresponds to $N_{Exp}$ alerts may be determined to be the target onset threshold.

If at 563 $N_{Exp}$ is greater than $N_{Ref}$ (that is, more alerts are expected from the signal metric during the specified time), then at 565 at least the onset threshold TO may be decreased such as by a step size specified in a threshold test protocol. The alert onsets detection may be performed on the same signal metric during the specified time period, and corresponding reference alerts may be generated at 561. The threshold adjustment process may continue until $N_{Exp}$ alerts (or within a specified margin of $N_{Exp}$) are generated. The corresponding onset and reset thresholds may be determined at 566. In an example, the smallest onset threshold that corresponds to $N_{Exp}$ alerts may be determined to be the target onset threshold.

In an example, the onset and reset thresholds at 566 may be deemed to be the target onset and reset threshold at 470, and used for future alert generation. In an example, and as illustrated in FIG. 5, information about patient indications received at 450, such as one or more of a clinical event, a stable period, or an unstable period during a specified time, may be used to further adjust the onset or reset threshold determined at 566. At 567, the clinical events including the temporal information of the known clinical events may be compared to the alerts generated using the thresholds TO and TR as determined at 566. An alert is generally expected to be generated for the known clinical event. If at 567 no alert is generated within the time period of the clinical event, then the process is directed to step 565, where at least the onset threshold TO may be decreased such as by a decrement step size according to the threshold test protocol. A reduced onset threshold TO may result in a higher sensitivity to the clinical event, which may increase the likelihood of generating an alert for the clinical event.

If at 567 at least one alert is generated during the known clinical event, then the target onset threshold may be determined to be the smallest threshold corresponding to the detected known clinical event. Such a choice of threshold may allow the known clinical events to be detected with the high sensitivity (which corresponds to low onset threshold). Alternatively, the alerts generated may be compared to the known stable period at 568. During the stable period, no alert or no more than a specified acceptable number of alerts are expected to be generated. If at 568, more alerts than the specified acceptable number occur within the stable period, then the process is directed to step 564, where at least the onset threshold TO may be increased such as by an increment step size according to the threshold test protocol. An increased onset threshold TO may correspond to a lower sensitivity to target physiological events, which may decrease the likelihood of generating an alert during the stable period.

When no more than the specified acceptable number of alerts are generated within the known stable period, the target onset threshold may be determined to be the smallest threshold corresponding to the specified acceptable number of alerts. In an example where no alert is expected during the stable period, the target onset threshold may be determined to be the smallest threshold corresponding to no alert during the stable period.

The alert may also be compared against the known unstable period at 569. At least one alert is generally expected to be generated during the unstable period. If at 569 no alert, or fewer than a specified number of alerts, falls within the unstable period, then the process is directed to step 565, where at least the onset threshold TO may be decreased such as by a decrement step size according to the threshold test protocol. A reduced onset threshold TO may result in a higher sensitivity to the clinical event, which may increase the likelihood of generating an alert during the unstable period. In an example, the onset threshold TO may be gradually decreased until the resultant alert occurs earliest in time and is substantially close to the beginning of the known unstable period. The target onset threshold may be determined to be the smallest threshold corresponding to the earliest alert within the unstable period. In some examples, the target reset threshold may be determined based on the target onset threshold weighted by a scaling factor, such as $TR=\alpha \cdot TO$. In an example, $0<\alpha<1$ such as the reset threshold TR is less than the corresponding onset threshold TO. The target onset and reset thresholds thus determined may then be used for future alert generation at 470.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for managing alerts associated with a target physiological event in a subject, the system comprising:
    a physiological sensor circuit including a sense amplifier circuit to sense a physiological signal;
    a signal processor circuit configured to generate a signal metric trend from the sensed physiological signal;
    an alert management circuit coupled to the signal processor circuit, the alert management circuit including:
        a comparator circuit to detect from the signal metric trend (1) one or more alert onsets using an onset threshold and (2) one or more corresponding alert terminations using a reset threshold;
        an alert generator circuit to issue one or more alerts corresponding to the detected one or more alert onsets and one or more alert terminations, and to generate a reference alert characteristic, including an alert timing or an alert statistic, using timing information or a count of the previously issued one or more alerts; and
        a parameter adjuster circuit to iteratively adjust the onset or reset threshold, including:
            when the reference alert characteristic of the one or more alerts fails to satisfy a specified alert characteristic, adjust the onset or reset threshold until the reference alert characteristic of the one or more alerts corresponding to the adjusted onset or reset threshold satisfies the specified alert characteristic; and
            when the reference alert characteristic of the one or more alerts satisfies the specified alert characteristic, determine target onset and reset thresholds for presenting to a user or a process, and
    a user interface for generating a human-perceptible presentation of the one or more alerts.

2. The system of claim 1, further comprising a detector circuit configured to detect a heart failure event based on the one or more alert onsets and the corresponding one or more alert terminations.

3. The system of claim 1, wherein the human-perceptible presentation of the one or more alerts include:
    an alert number during a specified period of time;
    an alert duration;
    an indication of true alert or false alert; or
    a count of true or false alerts.

4. The system of claim 1, wherein the user interface is configured to receive user input including the specified alert characteristic.

5. The system of claim 1, wherein the parameter adjuster circuit is configured to adjust at least one of the onset or reset threshold according to a step-up or a step-down protocol.

6. The system of claim 1, wherein the specified alert characteristic includes one or more of:
    an alert number during a specified time period;
    an alert duration;
    an inter-alert interval;
    a false alert number;
    a true alert number;
    a temporal pattern of alerts;
    a statistical distribution of alerts during a specified time period;
    a statistical distribution of alert durations;
    a statistical distribution of false alert number or true alert number; or
    a statistical distribution of inter-alert intervals.

7. The system of claim 1, wherein the specified alert characteristic includes an expected number of alerts during a specified time period, and the alert generator circuit issues a reference number of alerts corresponding to the detected alert onsets and alert terminations within the specified time period, and wherein the parameter adjuster circuit is configured to:
    if the expected alert number is less than the reference alert number, increase at least the onset threshold until the alert generator circuit issues the expected number of alerts; or
    if the expected alert number is greater than the reference alert number, decrease at least the onset threshold until the alert generator circuit issues the expected number of alerts.

8. The system of claim 1, wherein the specified alert characteristic includes an expected false alert number during a specified time period, and the alert generator circuit issues a reference false alert number within the specified time period, and wherein the parameter adjuster circuit is configured to, if the expected false alert number is less than the reference false alert number, increase at least the onset threshold until the alert generator circuit issues expected false alert number.

9. The system of claim 1, wherein the specified alert characteristic includes an expected true alert number during a specified time period, and the alert generator circuit issues a reference true alert number within the specified time period, and wherein the parameter adjuster circuit is configured to, if the expected true alert number is greater than the reference true alert number, decrease at least the onset threshold until the alert generator circuit issues expected true alert number.

10. The system of claim 1, wherein the parameter adjuster circuit is configured to:
    receive information about a known clinical event during a specified time period;
    adjust at least the onset threshold until the alert generator circuit issues at least one alert temporally corresponding to the known clinical event; and
    determine the target onset threshold as the adjusted threshold corresponding to the known clinical event.

11. The system of claim 1, wherein the parameter adjuster circuit is configured to:
    receive information about a known stable period;

adjust at least the onset threshold until the alert generator circuit issues no more than a specified acceptable number of alerts within the known stable period; and determine the target onset threshold as the adjusted threshold corresponding to the specified acceptable number of alerts.

12. The system of claim 11, wherein the specified acceptable number of alerts within the known stable period is zero, and the parameter adjuster circuit is configured to determine the target onset threshold as the smallest threshold corresponding to no alert during the stable period.

13. The system of claim 1, wherein the parameter adjuster circuit is configured to:

receive information about a known unstable period including onset timing of the known unstable period;

adjust at least the onset threshold until the alert generator circuit generates an alert substantially close to the onset timing of the known unstable period; and determine the target onset threshold as the smallest threshold corresponding to the alert substantially close to the onset timing of the known unstable period.

14. The system of claim 1, wherein the parameter adjuster circuit is configured to receive information about a medical history of the subject, and to determine the target onset or reset threshold based on the subject's medical history.

15. The system of claim 14, wherein the parameter adjuster circuit is configured to determine the specified alert characteristic including an indication-based characteristic based on an association between the subject's medical history and expected alert characteristic; and determine the target onset or reset threshold using the indication-based alert characteristic.

16. A method for managing alerts associated with a target physiological event in a subject via an alert management system, the method comprising:

sensing a physiological signal;

generating a signal metric trend from the sensed physiological signal;

detecting from the signal metric trend (1) one or more alert onsets using an onset threshold and (2) one or more corresponding alert terminations using a reset threshold;

issuing one or more alerts corresponding to the detected one or more alert onsets and one or more alert terminations;

generating a reference alert characteristic; including an alert timing or an alert statistic, using timing information or a count of the previously one or more alerts; and iteratively adjusting the onset or reset threshold via the alert management system, the iterative adjustment including:

when the reference alert characteristic of the one or more alerts fails to satisfy a specified alert characteristic; adjusting the onset or reset threshold until the reference alert characteristic of the one or more alerts corresponding to the adjusted onset or reset threshold satisfies the specified alert characteristic; and when the reference alert characteristic of the one or more alerts satisfies the specified alert characteristic, determining target onset and reset thresholds for presenting to a user or a process; and generating a human-perceptible presentation of the one or more alerts.

17. The method of claim 16, further comprising receiving information about a known clinical event during a specified time period, wherein the iterative adjustment of the onset or reset threshold includes:

adjusting at least the onset threshold until at least one alert temporally corresponding to the known clinical event is issued; and determining the target onset threshold as the adjusted threshold corresponding to the known clinical event.

18. The method of claim 16, further comprising receiving information about a known stable period, wherein the iterative adjustment of the onset or reset threshold includes:

adjusting at least the onset threshold until no more than a specified acceptable number of alerts is issued within the known stable period; and determining the target onset threshold as the adjusted threshold corresponding to the specified acceptable number of alerts.

19. The method of claim 16, further comprising receiving information about a known unstable period including onset timing of the known unstable period, wherein the iterative adjustment of the onset or reset threshold includes:

adjusting at least the onset threshold until an alert substantially close to the onset timing of the known unstable period is issued; and determining the target onset threshold as the smallest threshold corresponding to the alert substantially close to the onset timing of the known unstable period.

20. The method of claim 16, further comprising receiving information about a medical history of the subject, wherein the iterative adjustment of the onset or reset threshold includes:

determining the specified alert characteristic including an indication-based alert characteristic based on an association between the subject's medical history and expected alert characteristic; and determining the target onset or reset threshold using the indication-based alert characteristic.

* * * * *